US006866437B2

(12) United States Patent
Gueret

(10) Patent No.: US 6,866,437 B2
(45) Date of Patent: Mar. 15, 2005

(54) DEVICE HAVING A MAGNETIC APPLICATOR AND/OR WIPER MEMBER

(75) Inventor: Jean-Louis Gueret, Paris (FR)

(73) Assignee: L'Oreal, Paris (FR)

( * ) Notice: Subject to any disclaimer, the term of this patent is extended or adjusted under 35 U.S.C. 154(b) by 12 days.

(21) Appl. No.: 09/790,794

(22) Filed: Feb. 22, 2001

(65) Prior Publication Data

US 2001/0033766 A1 Oct. 25, 2001

(30) Foreign Application Priority Data

Mar. 3, 2000 (FR) .............................................. 00 02757

(51) Int. Cl.[7] .............................................. A45D 33/00
(52) U.S. Cl. ........................ 401/130; 401/122; 401/126
(58) Field of Search ................................ 401/118, 119, 401/123–127, 130

(56) References Cited

U.S. PATENT DOCUMENTS

| 1,968,475 | A | | 7/1934 | Beckwith et al. |
| 3,325,845 | A | | 6/1967 | Sawkiw |
| 3,428,043 | A | | 2/1969 | Shepherd |
| 3,499,446 | A | | 3/1970 | Tsuneizumi et al. |
| 4,156,067 | A | | 5/1979 | Gould |
| 4,337,859 | A | | 7/1982 | Murphy et al. |
| 4,377,160 | A | | 3/1983 | Romaine |
| 4,427,001 | A | * | 1/1984 | Kiefer et al. ................. 601/17 |
| 4,464,535 | A | | 8/1984 | Szantay et al. |
| 4,548,861 | A | | 10/1985 | Barnes et al. |

(List continued on next page.)

FOREIGN PATENT DOCUMENTS

| DE | 1 629 523 | 2/1971 |
| DE | (U) 86 10 769 | 4/1986 |
| DE | 3613280 | 10/1987 |
| DE | 3619987 | 12/1987 |
| DE | 3619987 A1 | 12/1987 |
| DE | 86 10 769 | 1/1994 |
| DE | 43 25 071 | 1/1995 |
| DE | 44 46 380 | 1/1996 |
| DE | 195 34 368 | 3/1997 |
| DE | 197 15 477 | 10/1998 |

(List continued on next page.)

OTHER PUBLICATIONS

French Search Report dated Nov. 29, 2000.
Minolta brochure, "Precise Color Communication", 1994.
Minolta brochure, "Spectrophotometer CM–2002", 1991.
Co–pending Application, Title: Device for Applying a Product and Method for Manufacturing Device, Inventor: Jean–Louis H. Gueret, filed Mar. 12, 2002.
Co–pending U.S. Appl. No. 09/541,464; Title: Patch with a Magnetic Field Effect, Inventor: Jean–Louis H. Gueret, filed Mar. 31, 2000.
English Language Derwent Abstract of EP 0 528 705, Feb. 24, 1993.
English Language Derwent Abstract of EP 0 764 441, Mar. 26, 1997.
English Language Derwent Abstract of DE 1 629 523, Feb. 4, 1971.

(List continued on next page.)

*Primary Examiner*—Gregory L. Huson
*Assistant Examiner*—Huyen Le
(74) *Attorney, Agent, or Firm*—Finnegan, Henderson, Farabow, Garrett & Dunner, LLP

(57) ABSTRACT

A device for applying a substance, in particular a cosmetic, the device comprising an applicator having a structure for application purposes and capable of transporting the substance onto a surface to be treated, and optionally a wiper member for wiping said applicator prior to applying the substance, wherein inside at least a portion of said structure and/or the wiper member there are disposed one or more elements generating or suitable for generating a magnetic field of predetermined orientation.

88 Claims, 5 Drawing Sheets

U.S. PATENT DOCUMENTS

| | | | |
|---|---|---|---|
| 4,571,768 A | 2/1986 | Kawashima | |
| 4,585,797 A | 4/1986 | Cioca | |
| 4,631,227 A | 12/1986 | Nakamura | |
| 4,643,939 A | 2/1987 | Sugiyama et al. | |
| 4,692,047 A * | 9/1987 | Endo | 401/141 |
| 4,724,138 A | 2/1988 | Duffy et al. | |
| 4,804,538 A | 2/1989 | Chen | |
| 4,814,167 A | 3/1989 | Wirth et al. | |
| 4,927,281 A | 5/1990 | Gueret | |
| 4,940,350 A | 7/1990 | Kim | 401/209 |
| 4,958,402 A | 9/1990 | Weihrauch | |
| 4,993,440 A | 2/1991 | Gueret | |
| 5,026,552 A | 6/1991 | Gueret et al. | |
| 5,049,376 A | 9/1991 | Murphy et al. | |
| 5,100,672 A | 3/1992 | Gueret et al. | |
| 5,161,554 A | 11/1992 | Fitjer | |
| 5,232,707 A | 8/1993 | Lokensgard | |
| 5,269,040 A | 12/1993 | Switall | |
| 5,349,972 A | 9/1994 | Dirksing et al. | |
| 5,357,647 A | 10/1994 | Gueret | |
| 5,374,429 A | 12/1994 | Kinoshita et al. | |
| 5,386,278 A | 1/1995 | Maeyama et al. | |
| 5,427,120 A * | 6/1995 | Wong | 132/120 |
| 5,466,456 A | 11/1995 | Glover | |
| 5,466,724 A | 11/1995 | Volke et al. | |
| 5,512,277 A | 4/1996 | Uemura et al. | |
| 5,567,072 A | 10/1996 | Dunleavy et al. | |
| 5,653,970 A | 8/1997 | Vermeer | |
| 5,702,713 A | 12/1997 | Joulia | |
| 5,762,432 A | 6/1998 | Dunleavy et al. | |
| 5,798,110 A | 8/1998 | Joulia | |
| 5,799,356 A | 9/1998 | Kawashima | |
| 5,800,835 A | 9/1998 | Zastrow et al. | |
| 5,811,107 A | 9/1998 | Gangadharan et al. | |
| 5,861,165 A | 1/1999 | Joulia | |
| 5,919,490 A | 7/1999 | Zastrow et al. | |
| 5,935,596 A | 8/1999 | Crotty et al. | |
| 5,958,443 A | 9/1999 | Viegas et al. | |
| 5,961,988 A | 10/1999 | Zastrow et al. | 424/400 |
| 5,987,691 A | 11/1999 | Jurt et al. | |
| 6,039,487 A | 3/2000 | Kristiansen | |
| 6,073,634 A | 6/2000 | Gueret | |
| 6,079,087 A | 6/2000 | Cansler | |
| 6,096,333 A | 8/2000 | Rolf et al. | |
| 6,163,918 A | 12/2000 | Weihrauch | |
| 6,174,600 B1 | 1/2001 | Brown et al. | |
| 6,269,514 B1 | 8/2001 | Edwards et al. | |
| 6,305,861 B1 | 10/2001 | Gueret | |
| 6,305,863 B1 * | 10/2001 | Gueret | 401/126 |
| 6,309,124 B1 * | 10/2001 | Gueret | 401/124 |
| 6,311,359 B1 | 11/2001 | Brezler, III | |
| 6,343,607 B1 * | 2/2002 | Gueret | 132/218 |
| 6,453,909 B1 * | 9/2002 | De Laforcade | 132/208 |
| 6,475,553 B2 | 11/2002 | Guay et al. | |
| 6,675,812 B1 * | 1/2004 | Wiley | 132/108 |
| 2001/0003600 A1 | 6/2001 | Guay | |

FOREIGN PATENT DOCUMENTS

| | | |
|---|---|---|
| DE | 197 15 478 | 10/1998 |
| EP | 0 063 875 | 11/1982 |
| EP | 0 191 198 | 6/1986 |
| EP | 1 190 814 | 8/1986 |
| EP | 0 309 309 | 3/1989 |
| EP | 0 412 869 | 2/1991 |
| EP | 0 528 705 | 2/1993 |
| EP | 0 651 984 | 5/1995 |
| EP | 0 764 411 | 3/1997 |
| EP | 1 043 018 A1 | 10/2000 |
| EP | 1 099 394 | 5/2001 |
| FR | 1 520 770 | 4/1968 |
| FR | 2 276 030 | 1/1976 |
| FR | 2 515 651 | 5/1983 |
| FR | 2 538 247 | 6/1984 |
| FR | 2 519 580 | 7/1984 |
| FR | 2 607 372 | 6/1988 |
| FR | 2 627 068 | 8/1989 |
| FR | 2 687 055 | 8/1993 |
| FR | 2 738 744 | 3/1997 |
| FR | 2 750 050 | 12/1997 |
| FR | 2 776 518 | 10/1999 |
| GB | 2 265 086 | 9/1993 |
| GB | 2 307 862 | 6/1997 |
| JP | 54-158007 U | 11/1979 |
| JP | 55-30453 | 3/1980 |
| JP | 61-112602 | 5/1986 |
| JP | 61-141307 | 6/1986 |
| JP | 61-187808 | 8/1986 |
| JP | 7-197311 | 8/1995 |
| JP | 10-324614 | 12/1998 |
| JP | 11-113638 | 4/1999 |
| JP | 11-504555 | 4/1999 |
| JP | 11-555635 | 6/1999 |
| JP | 2001-178541 | 7/2001 |
| WO | WO 87/05206 | 9/1987 |
| WO | WO92/14435 | 9/1992 |
| WO | WO 94/02674 | 2/1994 |
| WO | WO 94/17837 | 8/1994 |
| WO | WO 94/22423 | 10/1994 |
| WO | WO 95/05204 | 2/1995 |
| WO | WO 95/28136 | 10/1995 |
| WO | WO 96/14822 | 5/1996 |
| WO | WO 96/37283 | 11/1996 |
| WO | WO 98/31315 | 7/1998 |
| WO | WO 98/42303 | 10/1998 |
| WO | WO 99/42376 | 8/1999 |
| WO | WO 00/02468 | 1/2000 |

OTHER PUBLICATIONS

English Language Derwent Abstract of DE 3 613 280, Oct. 22, 1987.

English Language Derwent Abstract of DE 3 619 987, Dec. 17, 1987.

English Language Derwent Abstract of DE 44 46 380, Jan. 11, 1996.

English Language Derwent Abstract of DE 197 15 477, Oct. 15, 1998.

English Language Derwent Abstract of FR 1 520 770, Apr. 12, 1968.

English Language Derwent Abstract of FR 2 276 030, Jan. 23, 1976.

English Language Derwent Abstract of FR 2 519 580, Jul. 18, 1984.

English Language Derwent Abstract of FR 2 538 247, Jun. 29, 1984.

English Language Derwent Abstract of FR 2 738 744, Mar. 21, 1997.

English Language Derwent Abstract of FR 2 750 050, Dec. 26, 1997.

English Language Derwent Abstract of FR 2 776 518, Oct. 1, 1999.

English Language Derwent Abstract of JP 10–324614, Dec. 8, 1998.

English Language Derwent Abstract of JP 61–112602, May 30, 1986.

English Language Translation of JP 61–187808, Aug. 21, 1986.

English Language Derwent Abstract of JP 2001–178541, Jul. 3, 2001.
Patent Abstract of Japan 55081809, Jun. 20, 1980.
Patent Abstract of Japan 05168530, Jul. 2, 1993.
Patent Abstract of Japan 06179411, Jun. 28, 1994.
Patent Abstract of Japan 11113638, Apr. 27, 1999.
Patent Abstract of Japan 2000175942, Jun. 27, 2000.
Japanese Patent Application of H10–167928, Jun. 23, 1998.
Japanese Patent Application of H10–245319, Sep. 14, 1998.
Japanese Patent Application of H10–287587, Oct. 27, 1998.
Co–pending U.S. Appl. No. 09/709,397; Title: Applicator Device and System Having Particle–Laden Bristles, Method for Applying Product, and Method of Making Particle–Laden Bristles, Inventor(s): Jean–Louis H. Gueret, filed Nov. 13, 2000, Amendment filed Jan. 11, 2002, Amendment filed Jun. 21, 2002, Response to Election of Species Requirement filed Aug. 30, 2002, Amendment filed Feb. 10, 2003.
Co–pending U.S. Appl. No. 10/161,726; Title: Fiber and Device For Applying A Product, and Method of Manufacturing Device, Inventor(s): Jean–Louis H. Gueret, filed Jun. 5, 2002.
English language Derwent Abstract of DE 195 34 368, Mar. 20, 1997.

English language Derwent Abstract of EP 1 099 394, May 16, 2001.
English Language Derwent Abstract of EP 1 043 018, Oct. 11, 2000.
English language translation of Japanese Patent Application H10–167928, Jun. 23, 1998.
English language translation of Japanese Patent Application H10–245319, Sep. 14, 1998.
English language translation of Japanese Patent Application H10–287587, Oct. 27, 1998.
Patent Abstracts of Japan JP 11–113638, Apr. 27, 1999.
English language translation of Japanese Patent Application 11–113638, Apr. 27, 1999.
English language Derwent Abstract of JP 55–30453, Mar. 4, 1980.
English language Derwent Abstract of JP 7–197311, Aug. 1, 1995.
English language Derwent Abstract of JP 11–555635, Jun. 15, 1999.

* cited by examiner

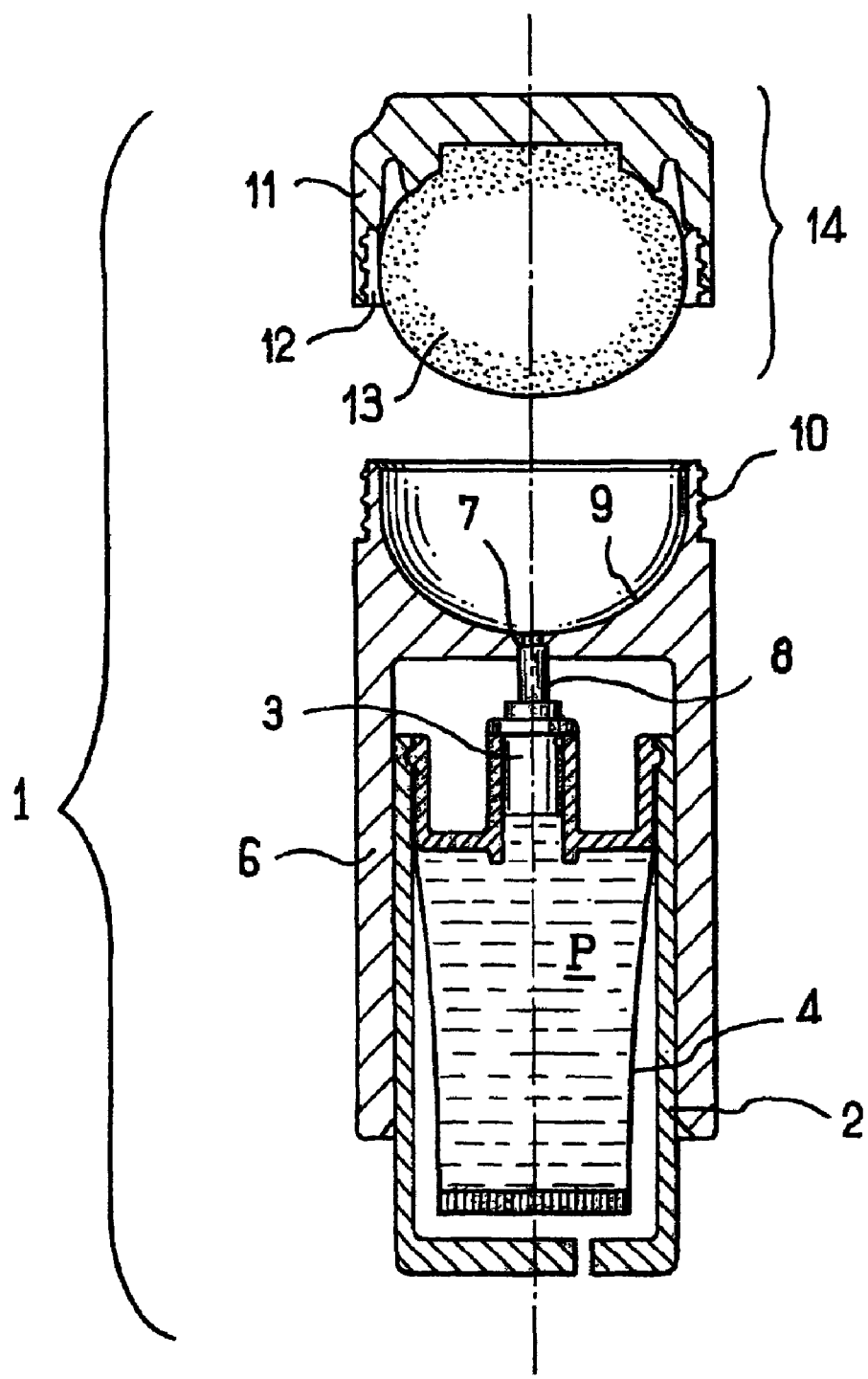
FIG_1

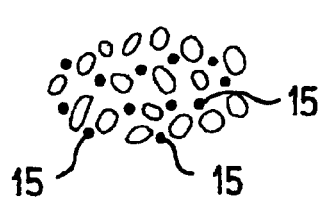
FIG_2
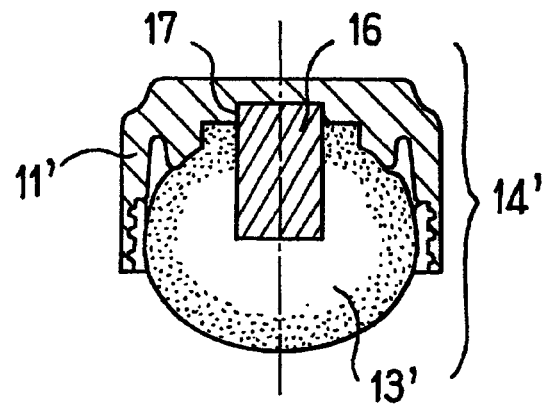
FIG_3
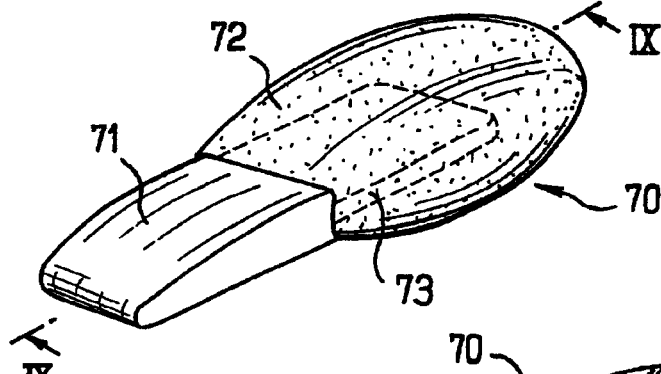
FIG_8
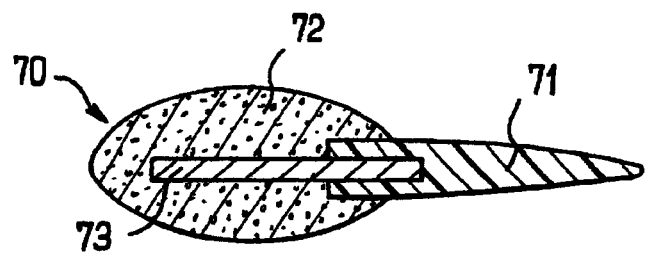
FIG_9
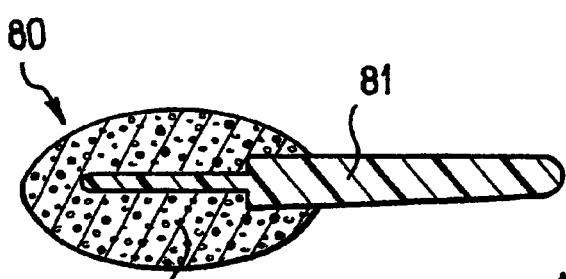
FIG_10
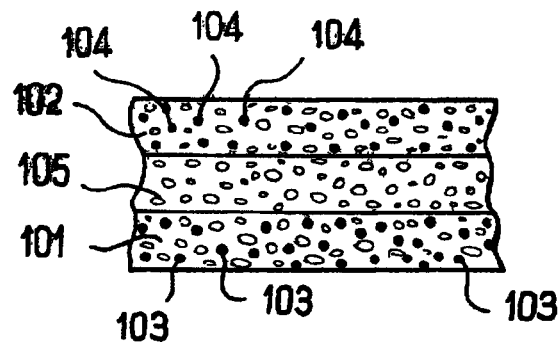
FIG_11

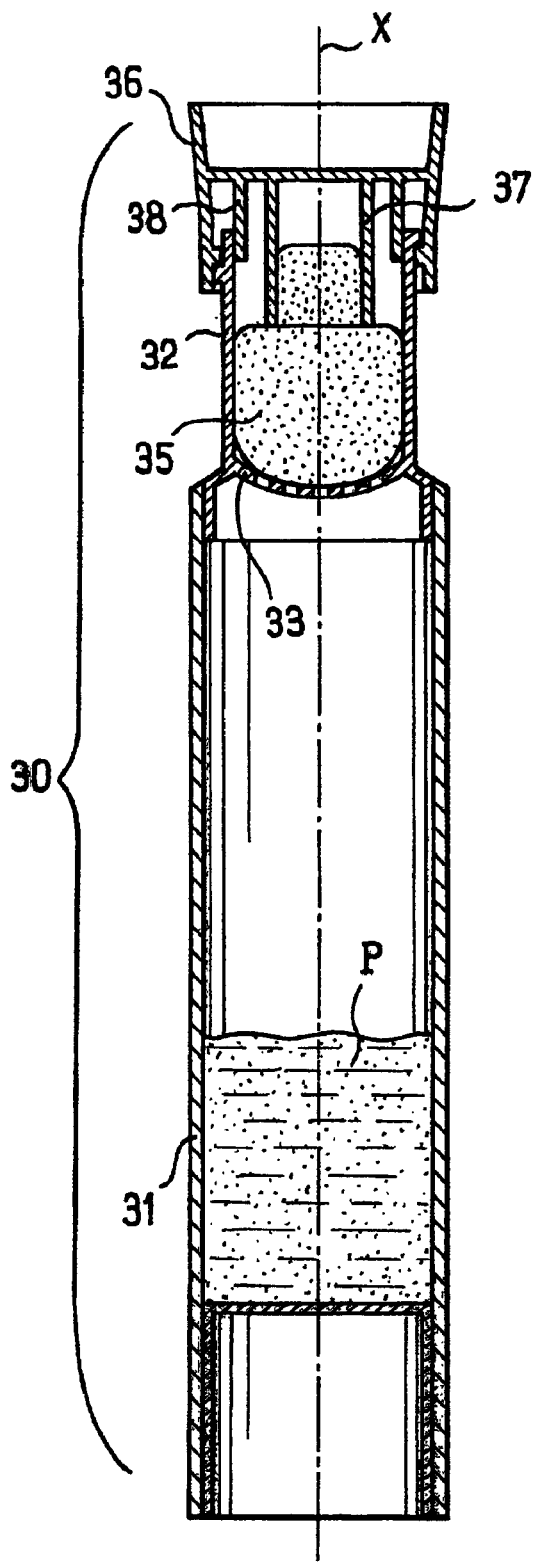
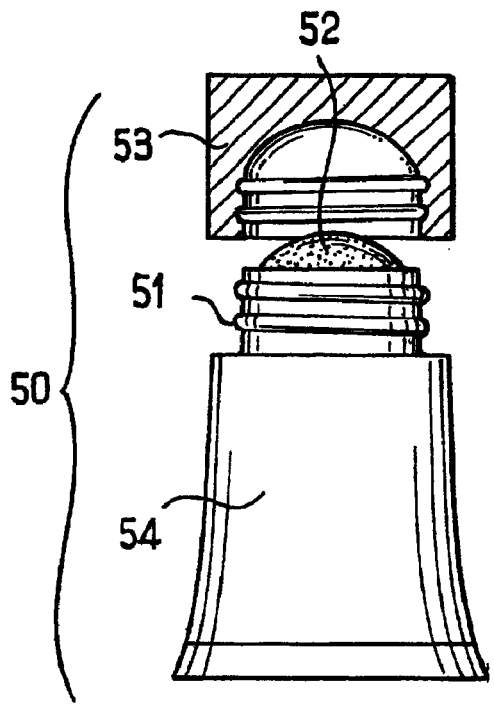
FIG_5
FIG_6

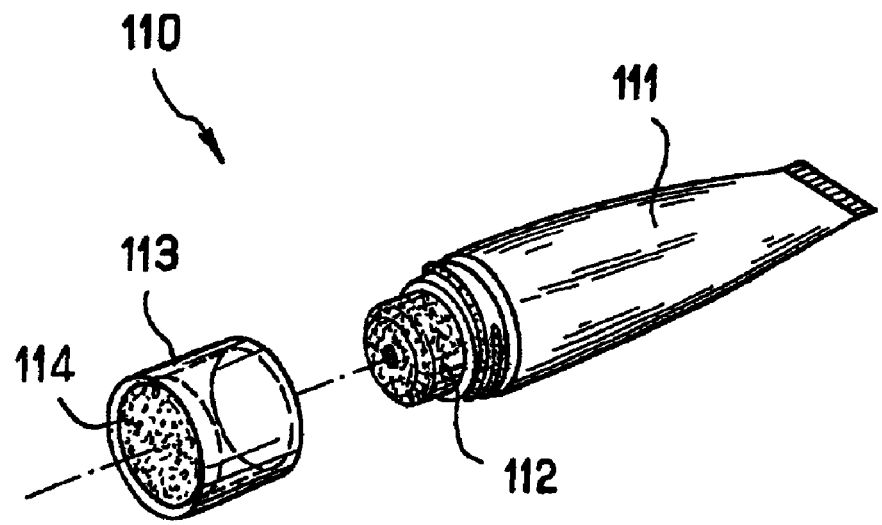
FIG_12
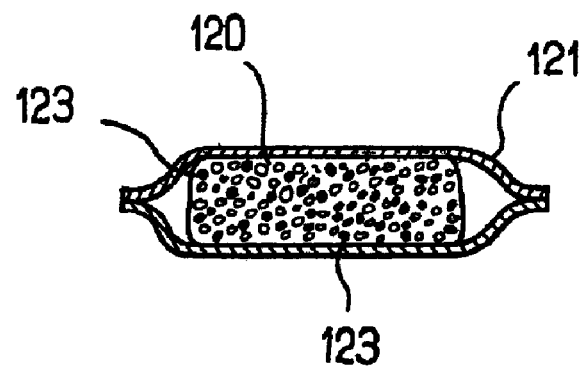
FIG_13

DEVICE HAVING A MAGNETIC APPLICATOR AND/OR WIPER MEMBER

The present invention relates to applying a substance, in particular a cosmetic, on a region of the body, or the face, or the hair.

BACKGROUND OF THE INVENTION

It is becoming more and more common for cosmetics to incorporate one or more care agents for the treated surface.

For example, these can be anti-wrinkle or moisturizing agents.

There exists a need in particular to encourage penetration of such agents, thereby reinforcing their effectiveness.

Patent application DE 4 325 071 proposes using magnetic particles for enhancing microcirculation.

In that prior application, the particles are dispersed in a cream, lotion, or gel, or they are placed on a bandage.

A problem which arises when magnetic particles are used is their tendency to clump together.

Publication WO 92/14435 discloses a massage device having a head in which a magnet can be integrated.

The head is not designed to be capable of being loaded with a substance to a certain depth and then to transfer the substance onto the surface to be treated.

OBJECTS AND SUMMARY OF THE INVENTION

The invention seeks in particular to resolve this problem and it provides a novel device for applying a substance, in particular a cosmetic, the device comprising an applicator having a structure for application purposes and capable of transporting the substance onto a surface to be treated, and optionally also a wiper member for wiping said applicator prior to applying the substance, which device is capable of using a magnetic field to exert a beneficial action on the treated surface, e.g. on microcirculation or on other aspects of the metabolism.

The invention achieves this by the fact that inside at least a portion of said structure and/or the wiper member there are disposed one or more elements generating or suitable for generating a magnetic field of predetermined orientation.

One or more such elements can be constituted by one or more magnets and/or magnetic particles and/or magnetizable particles.

In the meaning of the present application, the application structure must be understood as being the structure suitable for being loaded with a substance for application, in particular to some greater or lesser depth, and for transferring substance onto a surface to be treated when the structure is moved over and/or pressed against said surface.

On application, the application structure retains its own integrity.

The device of the invention advantageously has a self-contained unitary structure, i.e. it is not connected by means of a hose to a receptacle or by means of an electric cable to a power supply, unlike the device described in application WO 92/14435.

In the invention, the elements that generate, or are suitable for generating, a magnetic field of predetermined orientation are placed within the core of the applicator structure.

The depth to which the substance penetrates into the structure that is used for application depends on the nature of the structure, and it can be restricted to the thickness of flocking, for example.

When the applicator is magnetic, the invention makes it possible to enhance penetration of one or more active agents contained in the substance by improving microcirculation in the vicinity of the applicator.

The invention also makes it possible to use magnetic particles without fearing that they will dump together, since the particles are immobilized within the structure that is used for applying the substance.

Because it is exposed to the magnetic field, the substance present in the applicator can acquire additional properties, for example it can become polarized and it can present increased penetration power.

When only the wiper member is magnetic, such additional properties can be acquired on passing through the wiper member.

In a preferred embodiment, the above-mentioned structure has one or more magnets and/or magnetic particles and/or magnetizable particles.

Advantageously, the device has a receptacle and the applicator is arranged to take the substance from the receptacle.

In a particular embodiment, the applicator is arranged so that the substance can be pumped into the structure that is used for application purposes.

In another particular embodiment, the structure used for applying the substance is arranged in such a manner as to have the substance coming from the receptacle pass therethrough.

In yet another particular embodiment, the structure for applying the substance is preimpregnated in substance, in which case the applicator is packaged, for example in a leakproof envelope and serves as a sample.

Advantageously, the structure for applying the substance and/or the wiper member is/are porous, at least in part.

In a preferred embodiment, the above-specified structure and/or the wiper member is/are entirely porous.

The structure used for applying the substance and/or the wiper member are advantageously made of at least one material selected from the following list: foam, sponge, sintered block, aggregate of natural or synthetic fibers, woven or non-woven fibers, or a combination of such materials.

Advantageously, magnetic and/or magnetizable particles are used that are incorporated in such a material while it is being made, thereby making it possible to cause the magnetic and/or magnetizable particles to adhere or bind intimately with the fibers or cells of said material.

This ensures that the magnetic and/or magnetizable particles remain secured to the material constituting the structure used for applying the substance and do not run the risk of escaping from the applicator or the wiper member so as to become deposited on the treated surface, which could be a source of discomfort.

In a particular embodiment, the structure used for applying the substance and/or the wiper member comprise a foam or sponge having at least 10% open cells.

The thickness of such a structure can be at least a few millimeters, for example at least 5 mm.

The structure used for applying the substance and/or the wiper member can have flocking and/or roughness on the surface.

Advantageously, the structure used for applying the substance is fixed to a support, in particular by injecting material thereover, or by heat-sealing, or by adhesive.

Such a support can serve as a handle.

The support can have one or more magnets and/or magnetic particles, for example in order to reinforce the magnetic field exerted on the treated surface and/or to generate magnetic fields of different orientations.

The magnetic serving for applying the substance and/or the wiper member preferably include particles that are dispersed, advantageously in substantially uniform manner.

The particles can be dispersed uniformly as a result of the particles being incorporated in the material which is used for making the structure for applying the substance and/or the wiper member in the non-magnetized state, during manufacture of said material.

The structure used for applying the substance and/or the wiper member can have 0.2% to 80% by weight of magnetic particles.

The structure used for applying the substance and/or the wiper member can comprise an assembly of a plurality of types of porous materials so as to confer on the applicator stiffness, for example, that varies between zones, and so as to enable a surface to be treated differently as a function of which portion of the applicator is used for applying such treatment.

The structure for applying the substance and/or the wiper member can have magnetic particles and/or magnets arranged in such a manner as to generate magnetic fields of different orientations.

In particular, when a plurality of porous materials are used that are assembled together to make up the wiper member or the structure used for applying the substance, it is possible to incorporate magnetic particles and/or magnets in each of these materials so as to generate a field of predetermined orientation, and to combine the various materials so as to obtain a desired resultant field.

The magnetic particles used can be ferrites, in particular ferromagnetic ferrites having a high coercive field.

It is also possible to use paramagnetic ferrites situated in the vicinity of a magnet that generates a magnetic field for magnetizing the particles.

The invention also provides a method of manufacturing an applicator or a wiper member for wiping an applicator, the method comprising the following steps:

a) incorporating magnetizable particles within the wiper member or the applicator structure of the applicator; and b) subjecting said particles to a magnetic field in such a manner as to cause said structure to generate or be suitable for generating at least one magnetic field of predetermined orientation.

The magnetic field for magnetizing the magnetizable particles can be generated by a magnet that forms part of the applicator, thereby avoiding any need to subject the applicator or the wiper member to a magnetizer.

By introducing the particles in the non-magnetized state into the porous structure, the drawbacks associated with the risk of particles agglomerating because they are magnetic can be avoided.

BRIEF DESCRIPTION OF THE DRAWINGS

Other characteristics and advantages of the present invention will appear on reading the following detailed description of non-limiting embodiments, and on examining the accompanying drawings, in which:

FIG. 1 is a diagrammatic axial section view of a device constituting a first embodiment of the invention;

FIG. 2 is a diagrammatic view on a larger scale showing the foam of the FIG. 1 applicator;

FIG. 3 is a diagrammatic axial section view showing a variant embodiment of the applicator;

FIGS. 4 to 7 show various embodiments of devices of the invention;

FIG. 8 shows an applicator on its own and in diagrammatic manner;

FIG. 9 is a section on section line IX—IX of FIG. 8;

FIG. 10 is a diagrammatic section view showing a variant embodiment of an applicator;

FIG. 11 is a diagrammatic view on a larger scale showing a porous structure constituting a variant implementation of the invention;

FIG. 12 shows a variant embodiment of a device of the invention; and

FIG. 13 shows an applicator contained in an envelope prior to use.

MORE DETAILED DESCRIPTION

Figure 4:
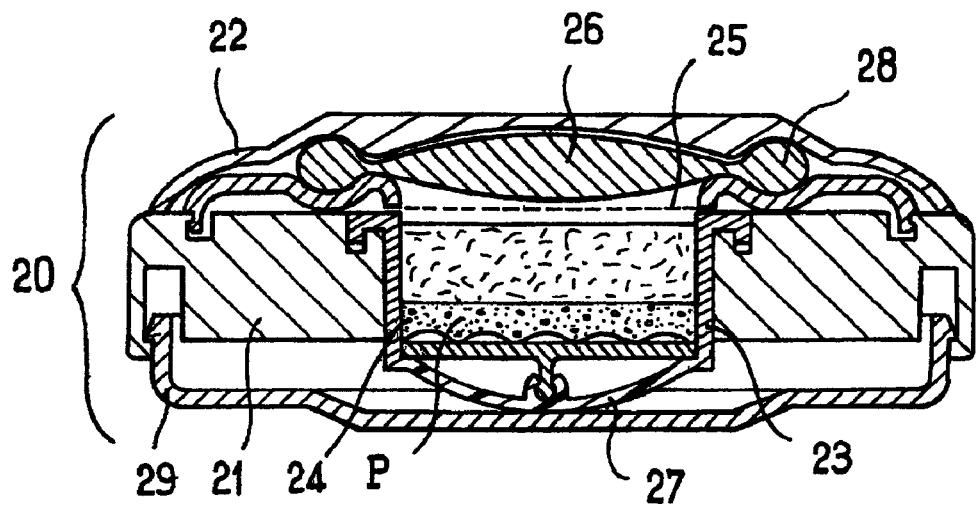

FIG. 1 shows a packaging and applicator device 1 comprising a body 2 having an airless pump 3 mounted thereon. This pump 3 is arranged to pump a substance P, a cosmetic or a care product, contained in a flexible bag 4 received inside the body 2.

The substance P can be water-based or oil-based, and it can contain active agents, e.g. agents which are hydrosoluble or liposoluble.

A sliding cover 6 is mounted on the body 2. The cover 6 has an externally-threaded neck 10 at its top end, and inside the neck it has an upwardly-open, substantially hemispherical recess 9.

The packaging and applicator device 1 also has an applicator 14 comprising a closure cap 11 provided with an assembly skirt 12 arranged to screw onto the threaded neck 10, together with an applicator structure 13 constituted by an open-celled natural rubber (NR) foam fixed inside the closure cap 11 and projecting downwards therefrom so as to be suitable for application to the skin.

The closure cap 11 serves as a support and as a handle.

In the bottom of its recess 9, the cover 6 has a through orifice with a shoulder 7 against which the rod 8 of the pump 3 comes to bear.

The threaded neck 10 and the assembly skirt 12 are arrange to co-operate in leakproof manner when the closure cap 11 is in place, such that the applicator 14 is then prevented from drying out.

In its bulk, the applicator structure 13 includes magnetic particles.

More precisely, the foam constituting the applicator structure 13 includes particles 15 distributed throughout its substance in substantially uniform manner, as shown in FIG. 2.

Such particles 15 are constituted, for example, by ferromagnetic particles such as ferrites, in particular ferrites based on zinc and manganese, etc., that are capable of retaining a considerable amount of remanent magnetization.

In the example described, these particles 15 are coated in an inert coating of polyurethane.

In a variant, they could be coated in an elastomer, in epoxy, in polyester, in polyamide, in urea-formaldehyde resin, or in cyanoacrylate, for example, in order to protect them from oxidizing and in order to give them a different color, in particular the same color as the application structure 13 so that they do not show up.

The particles 15 are introduced into the foam during manufacture thereof while they are in the non-magnetized state and they are subsequently magnetized after the chemical reaction that produces the foam has terminated.

To make the applicator structure 13, it is possible to start from a slab of foam that includes magnetizable particles.

The slab of foam can be magnetized as a whole after it has been manufactured and then cut up to form application structures 13.

In a variant, the slab of foam can be cut up to form application structures 13 before the magnetizable particles have been magnetized.

The applicator 14 is then magnetized separately, after it has been made.

The particles 15 present in the foam can be magnetized by being subjected to a magnetic field generated by a magnetizer of the kind listed in the catalog from Technique et Matériel Magnétique (TE2M) under the references CE500, PM 1000, or PM 2500, which are devices of medium to high power and capable of magnetizing magnets of a variety of grades and shapes at a high rate.

After magnetization, the particles 15 behave individually like respective unit magnets, generating a magnetic field of predetermined orientation, that depends on magnetization conditions.

In a variant, as shown in FIG. 3, an applicator 14' is used in which the applicator structure 13 of the applicator 14 is replaced by an applicator structure 13' that contains magnetic particles, and by a permanent magnet 16 which is fixed to the closure cap 11', which differs from the above-described cap 11 in that it has a setback 17 in which the magnet 16 is fixed.

The presence of the magnet serves to increase the intensity of the magnetic field exerted by the applicator 14' when it has magnetic particles 15 as in the preceding example.

The magnet 16 also makes it possible to generate a magnetic field of orientation that is different from that of the magnetic field produced by the magnetic particles contained in the applicator 13'.

In a variant embodiment, the applicator structure 13' is replaced by an applicator structure that does not contain any magnetic particles, with the field being generated by the magnet 16 alone.

In another variant embodiment, the applicator structure 13' is replaced by an applicator structure having magnetizable particles for being magnetized by the magnet 16, for example in order to avoid the need to subject these particles to a magnetizing magnetic field as generated by a magnetizer.

Because of the presence of the magnet 16, it is also possible to use paramagnetic particles and/or a combination of paramagnetic and/or ferromagnetic particles.

The invention is not limited to the use of ferrites, and it is possible to use paramagnetic particles of the kind sold by Cortex Biochem under the name Magacell or by Dynal under the name Dynabead.

In the embodiments of FIGS. 1 to 3, the applicator structure 13 or 13' is filled with substance under the effect of the pressure imparted to the substance by the pump 3, and possibly by a pumping effect when the applicator is withdrawn due to the foam expanding while the closure cap 11 or 11' is being unscrewed.

The invention is not limited to that type of applicator.

FIG. 4 shows a packaging and applicator device 20 comprising a compact having a body 21, a hinged lid 22, and a sliding wall 29.

The body 21 has a recess that receives a cup 23 containing a supply of substance P.

The cup 23 is provided on top with a screen 25 and has a bottom wall 27 that is deformable.

The piston 24 secured to the deformable wall 27 can slide inside the cup 23.

By pressing against the sliding wall 29, the user pushes the piston 24 upwards and expels substance through the screen 25.

An applicator 26 constituted by a sponge is received inside the lid 22 above the screen 25.

The packaging and applicator device 20 is preferably arranged, as in the example described, so as to store the applicator 26 under leakproof conditions.

For this purpose, the applicator 26 has its periphery secured to an annular bead 28 which provides a sealing gasket when it is clamped between the lid 22 and a cover mounted on the body 21, when the device 20 is closed.

The applicator 26 is thus prevented from drying out when the lid 22 is closed.

The central region of the applicator 26 constitutes an applicator structure capable of being filled with substance, and it incorporates a dispersion of magnetic particles suitable for generating a magnetic field of given orientation.

In a variant, the applicator 26 is replaced by an aggregate of natural or synthetic fibers.

FIG. 5 shows a dispenser and packaging device 30 comprising a receptacle 31 provided with an externally-threaded neck 32.

On the inside, the neck 32 has a perforated bottom wall 33.

This dispensing and packaging device 30 has an applicator which comprises an applicator structure 35 carried by a handle 36 which also constitutes a closure cap fitted to the neck 32.

The applicator structure 35 is partially engaged and fixed in an assembly skirt 37 of the cap 36.

The cap has a sealing skirt 38 shaped to fit in leakproof manner inside the neck 32 when the cap 36 is screwed onto the neck.

The applicator structure 35 is constituted by an open-celled polyurethane foam and it incorporates a dispersion of magnetic particles.

The applicator structure 35 can become filled with substance by capillarity.

FIG. 6 shows a dispensing and packaging device 50 that comprises a flexible tube 54 having a threaded neck 51, the neck being provided internally with an applicator 52 having an applicator structure constituted by a block of open-celled polyether foam The applicator 52 includes magnetic particles.

When not in use, the tube 54 is closed in leakproof manner by a closure cap 53.

To expel substance, the user squeezes the tube 54.

The substance is expelled through the applicator 52 which is permeable to the substance contained in the tube.

In a variant, the applicator 52 is replaced by sintered particles of plastics material (in particular polyethylene), of ceramic, of metal, or of glass, with such a sintered block having pores that communicate with one another in all directions.

Figure 7:
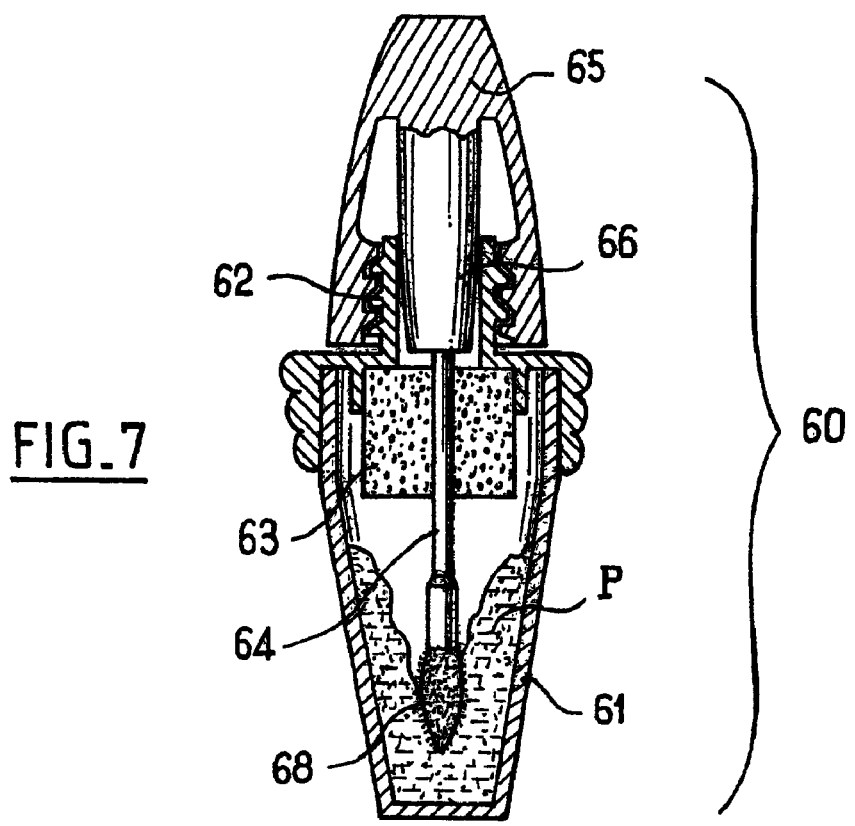

FIG. 7 shows a packaging and applicator device 60 comprising a receptacle 61 provided with an externally-threaded neck 62.

A wiper member 63 constituted by an axially-split block of open-celled polyurethane foam is fixed inside the receptacle 61 beneath the neck 62.

The receptacle 61 is closed by a closure cap 65 that is screwed onto the neck 62.

The closure cap 65 has a central portion 66 suitable for fitting in leakproof manner inside the neck 62.

The central portion 66 is extended downwards by a stalk 64 provided at its end with a flocked applicator 68.

The wiper member 63 serves to wipe the stalk 64 and the applicator 68 while being extracted from the receptacle 61.

The wiper member 63 has magnetic particles which subject the applicator 68 to a magnetic field while the applicator is being extracted from the receptacle 61.

This exposure to a magnetic field is liable to modify the substance as it passes through the wiper member, which modifications can, for example, enhance penetration of the active agent(s) at the moment of application.

FIGS. 8 and 9 show an applicator 70 comprising a support 71 of rigid or semi-rigid plastics material and an applicator structure 72, e.g. overmolded onto the support 71, the applicator structure 72 possibly also being flocked on its surface.

The support 71 is arranged to receive a magnetic core 73, e.g. constituted by a permanent magnet.

In a variant (not shown), the magnetic core 73 is replaced by an extension of the support 71 that has magnetic particles incorporated therein, e.g. ferrites.

In the example of FIGS. 8 and 9, the support 71 serves as a handle.

In a variant (not shown), the support 71 is replaced by a stalk like the stalk 64 of the packaging and applicator device 60 of FIG. 6.

FIG. 10 shows an applicator 80 comprising a support 81 and an applicator element 82 made of a porous material, e.g. a foam, that incorporates magnetic particles, e.g. ferrites.

The invention is not limited to a particular structure of applicator and, in particular, it is possible for the structure that retains substance for application purposes to be implemented in the form of a composite structure e.g. comprising a plurality of layers having different magnetic properties (as shown in FIG. 11), for example two porous layers 101 and 102 constituting top and bottom layers that contain respective magnetic particles 103 and 104 and that are separated by a porous layer 105 that is not magnetic.

The multilayer structure of FIG. 11 makes it possible to expose the surface to be treated to magnetic fields of different orientations providing the magnetic fields created by the particles 103 and 104 are of different orientations, and also to make an applicator of varying stiffness.

FIG. 12 shows a packaging and applicator device 110 comprising a tube 111 containing a substance such as a lotion and provided with an applicator comprising an applicator structure 112 constituted by a block of foam that incorporates magnetic particles.

The device 111 includes a closure cap 113 that houses a supply 114 of a substance that is capable of dispersing progressively on coming into contact with the substance contained in the tube 111.

The substance passes through the applicator structure 112 to be delivered and is then subjected to the magnetic field that is generated by the magnetic particles present within said structure.

FIG. 13 shows an applicator 120 contained in an envelope 121 prior to use and intended to serve as a sample, for example.

The applicator 120 in the example described is constituted by an open-celled foam containing magnetic particles 123 and impregnated in a substance.

By using magnetic particles or magnets, the invention makes it possible to exert a beneficial effect, in particular on oxygenating the skin and on microcirculation at the time the substance is applied to the skin, by subjecting the skin to the action of a magnetic field.

The effectiveness of the active agents contained in the applied substance is thus reinforced.

The magnetic field(s) generated can have a variety of orientations, and in particular the N-S polar axis can be perpendicular or parallel to the treated surface.

When the applicator structure is capable of deforming at the moment of application and when it contains magnetic particles, the orientation of the magnetic field can be modified under the effect of the applicator structure being deformed.

What is claimed is:

1. A device for applying a cosmetic substance, the device comprising:
    an applicator comprising an applicator structure configured to be loaded with the cosmetic substance and to apply the loaded cosmetic substance to one of skin and hair,
    wherein the applicator structure comprises a plurality of particles configured to generate a magnetic field, the particles being dispersed in the applicator structure, and
    wherein the applicator structure is nonbristled.

2. The device of claim 1, wherein the magnetic field has a predetermined orientation.

3. The device of claim 1, wherein at least a portion of the applicator structure is configured to absorb the cosmetic substance.

4. The device of claim 1, wherein the plurality of particles configured to generate a magnetic field comprises magnets.

5. The device of claim 1, wherein the plurality of particles configured to generate a magnetic field comprises magnetizable particles.

6. The device of claim 1, further comprising a receptacle for containing the cosmetic substance to be applied, wherein the applicator structure is configured to be loaded with cosmetic substance from the receptacle.

7. The device of claim 6, further comprising the cosmetic substance, wherein the cosmetic substance is contained in the receptacle.

8. The device of claim 6, wherein the cosmetic substance is intended for application to at least one of hair and skin.

9. The device of claim 6, further comprising a pump configured to pump the cosmetic substance from the receptacle to the applicator structure.

10. The device of claim 9, further comprising a recess in flow communication with the pump, the recess being configured to receive the applicator structure.

11. The device of claim 10, further comprising a cap configured to removably cover the recess.

12. The device of claim 11, wherein the applicator structure is attached to the cap.

13. The device of claim 1, further comprising a receptacle for containing the cosmetic substance to be applied, wherein the applicator structure is configured to be arranged relative to the receptacle so as to permit loading of the applicator structure with cosmetic substance from the receptacle.

14. The device of claim 1, wherein the applicator structure is preimpregnated with the cosmetic substance to be applied.

15. The device of claim 14, further comprising a sealed envelope, wherein the applicator is packaged in the sealed envelope.

16. The device of claim 1, wherein at least a portion of the applicator structure is porous.

17. The device of claim 1, wherein the applicator structure is made of at least one of a foam, a sponge, a sintered block, an aggregate of natural fibers, an aggregate of synthetic fibers, woven fibers, and non-woven fibers.

18. The device of claim 1, wherein the applicator structure is made of at least one of a foam and a sponge, the foam and the sponge each having at least 10% open cells.

19. The device of claim 1, wherein at least a portion of a surface of the applicator structure has at least one of a flocking and a roughness thereon.

20. The device of claim 1, further comprising a support member configured to hold the applicator structure.

21. The device of claim 20, wherein the applicator structure is fixed to the support member.

22. The device of claim 21, wherein the support member comprises a handle.

23. The device of claim 22, wherein the support member includes at least one of a magnet and a magnetic particle.

24. The device of claim 1, wherein the particles are dispersed in a substantially uniform manner throughout at least a portion of the applicator structure.

25. The device of claim 1, wherein the applicator structure comprises 0.2% by weight to 80% by weight of the particles.

26. The device of claim 1, wherein the applicator structure comprises a plurality of porous materials.

27. The device of claim 1, wherein the applicator structure comprises magnets arranged to generate magnetic fields of differing orientations.

28. The device of claim 1, wherein the plurality of particles configured to generate a magnetic field are coated in a material suitable for protection against at least one of oxidation and changing of color.

29. The device of claim 1, wherein the device is a self-contained one-piece structure.

30. The device of claim 1, wherein the plurality of particles configured to generate a magnetic field are disposed within at least a portion of the applicator structure.

31. A method of applying substance, the method comprising:
providing the device of claim 1,
loading at least a portion the applicator structure with the cosmetic substance; and
placing the loaded applicator structure in contact with a surface so as to apply the cosmetic substance.

32. The method of claim 31, wherein the placing of the loaded applicator structure in contact with the surface comprises placing the loaded applicator structure in contact with a surface on one of hair and skin.

33. The method of claim 31, wherein the loading of the applicator structure includes loading the applicator structure with cosmetic substance contained in a receptacle.

34. The method of claim 31, wherein the loading of the applicator structure includes preimpregnating the applicator structure with the cosmetic substance.

35. A device for applying a substance, the device comprising:
an applicator comprising an applicator structure configured to be loaded with the substance and to apply the loaded substance,
wherein the applicator structure comprises a plurality of particles configured to generate a magnetic field, the particles being dispersed in the applicator structure, an wherein at least part of the applicator structure comprises a porous material.

36. The device of claim 35, wherein the magnetic field has a predetermined orientation.

37. The device of claim 35, wherein the plurality of particles configured to generate a magnetic field comprises magnets.

38. The device of claim 35, wherein the plurality of particles configured to generate a magnetic field comprises magnetizable particles.

39. The device of claim 35, further comprising a receptacle for containing the substance to be applied, wherein the applicator structure is arranged to be loaded with substance from the receptacle.

40. The device of claim 39, further comprising the substance in the receptacle.

41. The device of claim 40, wherein the substance is a cosmetic substance.

42. The device of claim 41, wherein the substance is intended for application to at least one of hair and skin.

43. The device of claim 41, further comprising a pump configured to pump substance from the receptacle to the applicator structure.

44. The device of claim 43, further comprising a recess in flow communication with the pump, the recess being configured to receive the applicator structure.

45. The device of claim 44, further comprising a cap configured to removably cover the recess.

46. The device of claim 45, wherein the applicator structure is attached to the cap.

47. The device of claim 35, further comprising a receptacle for containing the substance to be applied, wherein the applicator structure is configured to be arranged relative to the receptacle so as to permit loading of the applicator structure with substance from the receptacle.

48. The device of claim 35, wherein the applicator structure is preimpregnated with the substance to be applied.

49. The device of claim 48, further comprising a sealed envelope, wherein the applicator is packaged in the sealed envelope.

50. The device of claim 35, wherein the applicator structure is made of at least one of a foam, a sponge, a sintered block, an aggregate of natural fibers, an aggregate of synthetic fibers, woven fibers, and non-woven fibers.

51. The device of claim 35, wherein the applicator structure is made of at least one of a foam and a sponge, the foam and the sponge each having at least 10% open cells.

52. The device of claim 35, wherein at least a portion of a surface of the applicator structure has at least one of a flocking and a roughness thereon.

53. The device of claim 35, further comprising a support member configured to hold the applicator structure.

54. The device of claim 35, wherein the applicator structure is fixed to the support member.

55. The device of claim 54, wherein the support member comprises a handle.

56. The device of claim 54, wherein the support member is configured to receive at least some of the plurality of particles configured to generate a magnetic field.

57. The device of claim 35, wherein the particles are dispersed in a substantially uniform manner throughout at least a portion of the applicator structure.

58. The device of claim 35, wherein the applicator structure comprises 0.2% by weight to 80% by weight of the particles.

59. The device of claim 35, wherein the applicator structure comprises a plurality of porous materials.

60. The device of claim 35, wherein the plurality of particles are configured to generate magnetic fields of differing orientations.

61. The device of claim 35, wherein the plurality of particles configured to generate a magnetic field are coated in a material suitable for protection against at least one of oxidation and changing of color.

62. The device of claim 35, wherein the device is a self-contained, integral structure.

63. The device of claim 35, wherein the applicator structure is configured to apply a cosmetic substance to the surface.

64. The device of claim 35, wherein the plurality of particles configured to generate a magnetic field are disposed within the applicator structure.

65. A method of applying substance, the method comprising:

provding the device of claim 35;

loading at least a portion of the applicator structure with the substance; and placing the loaded applicator structure in contact with a surface so as to apply the substance.

66. The method of claim 65, wherein the placing of the loaded applicator structure in contact with the surface comprises placing the loaded applicator structure in contact with a surface on one of hair and skin.

67. The method of claim 65, wherein the loading of the applicator structure includes loading the applicator structure with make-up substance.

68. The method of claim 65, wherein the loading of the applicator structure includes loading the applicator structure with substance contained in a receptacle.

69. The method of claim 65, wherein the loading of the applicator structure includes preimpregnating the applicator structure with the substance.

70. A method of manufacturing an applicator for applying a cosmetic substance, the method comprising:

providing an applicator comprising an applicator structure configured to be loaded with a cosmetic substance and to apply the loaded cosmetic substance, wherein the applicator structure comprises a plurality of magnetizable particles, and wherein the applicator structure is nonbristled; and subjecting the magnetizable particles to a magnetic field such that the particles generate at least one magnetic field of predetermined orientation.

71. The method of claim 70, further comprising associating the plurality of magnetizable particles with the applicator structure.

72. The method of claim 71, wherein the associating of the plurality of magnetizable particles comprises associating the plurality of magnetizable particles with the applicator structure when the magnetizable particles are in a non-magnetized state.

73. The method of claim 70, wherein the applicator further comprises a permanent magnet, and further wherein the subjecting the magnetizable particles to the magnetic field comprises subjecting the magnetizable particles to a magnetic field generated by the permanent magnet.

74. The method of claim 70, wherein at least a portion of the applicator structure is configured to absorb the substance.

75. A device for applying a substance, the device comprising:

an applicator comprising an applicator structure configured to be loaded with the substance and to apply the loaded substance, wherein the applicator structure comprises at least one element configured to generate a magnetic field; and a receptacle configured to contain the substance to be applied, the receptacle defining a recess configured to receive the applicator structure.

76. The device of claim 75, wherein at least a portion of the applicator structure is porous.

77. The device of claim 76, wherein the applicator structure comprises a plurality of magnetic particles.

78. The device of claim 76, further comprising the substance to be applied, wherein the substance is contained in the receptacle.

79. The device of claim 78, wherein the substance is a make-up substance.

80. The device of claim 76, wherein the applicator structure is configured to apply the substance to one of hair and skin.

81. The device of claim 75, further comprising a wiper member configured to wipe excess substance from the applicator structure.

82. A device for applying a substance, the device comprising:

an applicator comprising an applicator structure configured to be loaded with the substance and to apply the loaded substance, wherein the applicator structure comprises at least one element configured to generate a magnetic field; and a handling member configured to be grasped to hold the applicator structure, the handling member being configured to removably cover a receptacle containing the substance to be applied.

83. The device of claim 82, wherein at least a portion of the applicator structure is porous.

84. The device of claim 82, further comprising a wiper member configured to wipe excess substance from the applicator structure.

85. The device of claim 82, wherein the applicator structure comprises a plurality of magnetic particles.

86. The device of claim 82, further comprising the substance to be applied, wherein the substance is contained in the receptacle.

87. The device of claim 86, wherein the substance is a make-up substance.

88. The device of claim 82, wherein the applicator structure is configured to apply the substance to one of hair and skin.

* * * * *

UNITED STATES PATENT AND TRADEMARK OFFICE
CERTIFICATE OF CORRECTION

PATENT NO. : 6,866,437 B2
DATED : March 15, 2005
INVENTOR(S) : Jean-Louis H. Gueret It is certified that error appears in the above-identified patent and that said Letters Patent is hereby corrected as shown below:

Column 9,
Line 45, replace "claim 1," with -- claim 1; --;
Line 46, replace "portion the" with -- portion of the --; and
Line 67, replace "an" with -- and --.

Signed and Sealed this

Twenty-ninth Day of November, 2005

JON W. DUDAS
*Director of the United States Patent and Trademark Office*